(12) United States Patent
Bianchi et al.

(10) Patent No.: US 6,995,177 B1
(45) Date of Patent: Feb. 7, 2006

(54) HCV NS3 PROTEASE INHIBITORS

(75) Inventors: Elisabetta Bianchi, Rome (IT); Daniela Fattori, Genzano (IT); Paolo Ingallinella, Pomezia (IT); Antonello Pessi, Rome (IT)

(73) Assignee: Istituto Di Ricerche Di Biologia Molecolare P Angeletti SPA, Pomezia (IT)

( * ) Notice: Subject to any disclaimer, the term of this patent is extended or adjusted under 35 U.S.C. 154(b) by 503 days.

(21) Appl. No.: 10/129,421

(22) PCT Filed: Nov. 2, 2000

(86) PCT No.: PCT/GB00/04195

§ 371 (c)(1),
(2), (4) Date: Sep. 6, 2002

(87) PCT Pub. No.: WO01/32691

PCT Pub. Date: May 10, 2001

(30) Foreign Application Priority Data

Nov. 2, 1999 (GB) .................................... 9925955

(51) Int. Cl.
*A61K 38/06* (2006.01)
(52) U.S. Cl. ...................................... 514/331
(58) Field of Classification Search ................ 514/18, 514/331
See application file for complete search history.

(56) References Cited

FOREIGN PATENT DOCUMENTS

WO      WO 99/38888      8/1999

OTHER PUBLICATIONS

Ingallinella et al, "Potent Peptide Inhibitors of Human Hepatitis C Virus NS3 Protease Are Obtained by Optimizing the Cleavage Products," Biochemistry (1998), vol. 37, pp. 8906-8914.*
CDC Updates Guidelines for Prevention and Control of Infections with Hepatitis Viruses in Correctional Settings: http://www.aafp.org/afp/20030615/practice.html.*
Paolo Ingallinella, et al.; Biochemistry; vol. 37(25); pp. 8906-8914; 1998.

* cited by examiner

*Primary Examiner*—Bruce R. Campell
*Assistant Examiner*—Thomas S. Heard
(74) *Attorney, Agent, or Firm*—Kenneth R. Walton; Valerie J. Camara

(57) ABSTRACT

Compounds of formula (I) and pharmaceutically acceptable salts and esters thereof are active as inhibitors of hepatitis C virus NS3 protease. Consequently they are potentially useful in the treatment and prevention of hepatitis C virus infection and related conditions. In formula: (I) represents an aromatic or aliphatic carbocyclic ring and (n) is the total number of carbon atoms in the ring and is form 4 to 8.

23 Claims, No Drawings

HCV NS3 PROTEASE INHIBITORS

TECHNICAL FIELD

This invention relates to compounds which can act as inhibitors of the hepatitis C virus (HCV) NS3 protease, to uses of such compounds and to their preparation.

BACKGROUND ART

The hepatitis C virus (HCV) is the major causative agent of parenterally-transmitted and sporadic non-A, non-B hepatitis (NANB-H). Some 1% of the human population of the planet is believed to be affected. Infection by the virus can result in chronic hepatitis and cirrhosis of the liver, and may lead to hepatocellular carcinoma. Currently no vaccine nor established therapy exists, although partial success has been achieved in a minority of cases by treatment with recombinant interferon-α, either alone or in combination with ribavirin. There is therefore a pressing need for new and broadly-effective therapeutics.

Several virally-encoded enzymes are putative targets for therapeutic intervention, including a metalloprotease (NS2-3), a serine protease (N-terminal part of NS3), a helicase (C-terminal part of NS3), and an RNA-dependent RNA polymerase (NS5B). The NS3 protease is located in the N-terminal domain of the NS3 protein, and is considered a prime drug target since it is responsible for an intramolecular cleavage at the NS3/4A site and for downstream intermolecular processing at the NS4A/4B, NS4B/5A and NS5A/5B junctions.

Previous research has identified classes of peptides, in particular hexapeptides, showing degrees of activity in inhibiting the NS3 protease. The aim of the present invention is to provide further compounds which exhibit similar, and if possible improved, activity.

According to the nomenclature of Schechter & Berger (1967, Biochem. Biophys. Res. Commun. 27, 157–162) cleavage sites in substrates for the NS3 protease are designated P6-P5-P4-P3-P2-P1 . . . P1'-P2'-P3'-P4'-, with each P representing an amino acid, and the scissile bond lying between P1 and P1'. Corresponding binding sites on the enzyme are indicated as S6-S5-S4-S3-S2-S1 . . . S1'-S2'-S3'-S4'.

The present applicant has previously disclosed so called product inhibitors which are based on the P-region of the natural cleavage sites and which have been optimised to low nanomolar potency ((1998) Biochemistry 37: 8899–48905 and (1998) Biochemistry 37: 8906–8914. These inhibitors extract much of their binding energy from the C-terminal carboxylate, the remaining interactions with NS3 being similar to the ones used by the natural substrates, including binding in the $S_1$ pocket and the prominent electrostatic interaction of the P6-P5 acidic couple.

At variance with the P region, the P' region of the substrate, while being important for catalysis, does not influence significantly ground-state binding to the enzyme as expressed by the Km value. In other words, binding energy released by the substrate interaction with the enzyme to form an initial non-covalent complex is essentially due to the interaction of the residues of the P region; the P' region residues contribute to a lesser extent to the binding energy. Accordingly, peptides based on the P' region of the natural substrates (spanning residues $P_1'$–$P_{10}'$) do not inhibit NS3 to any significant extent. This notwithstanding, inspection of the crystal structure of NS3 with or without 4A (and more recently of the NMR structure of NS3) shows the presence of binding pockets in the S' region which might be exploited for the binding of active-site directed inhibitors. S'-binding ligands would therefore display a range of interactions with the enzyme different from the ones used by the substrate, and represent a novel class of NS3 inhibitors.

Landro et al in (1997) Biochemistry 36, 9340–9348 synthesized certain non-cleavable decapeptides based on the NS5A/5B cleavage site by substituting the $P_1'$ serine by a bulky cyclic aromatic (tetrahydroisoquinoline-3carboxylic acid) or smaller cyclic alkyl compound (proline or pipecolinic acid). They then investigated the interaction of these decapeptides with the substrate binding site of NS3 either in the presence or absence of NS4A cofactor. By looking at the effect of truncation at either the P or P' side of the molecule they concluded that most of the binding energy of the decapeptide is due to interactions with NS3–NS4A complex on the P side of the molecule. Truncation on the P' side produced a relatively large effect in the presence of NS4A cofactor, but less when NS4A was absent. They concluded that the P4' substrate Tyr residue present in their molecules was in close proximity, or in direct contact with NS4A and that this residue contributes significantly to binding in the presence of NS4A.

WO-A-00/31129 describes the development of inhibitors which are more powerful than those described by Landro et al because they have better binding on their P' side. In other words, the inhibitors take advantage of binding to the S' region in addition to binding to the S-region of NS3. By varying the P' amino acid residues, it was shown that the binding energy which may be extracted from S'-region binding is substantial, since inhibitors with optimised and non-optimised P'-regions differ in potency>1000-fold. Since no activity was present in any of the peptides corresponding to the isolated P'-region, optimisation of an S'-binding fragment was pursued in the context of non-cleavable decapeptides spanning $P_6$–$P_4'$.

Many of the compounds described in WO-A-00/31129 are oligopeptides, some including as many as ten amino acid residues. Peptidic molecules of this length may be unsuitable for peroral administration because they are subject to degradation in the digestive tract. Thus, it is desirable to develop shorter peptides or molecules having less peptidic character. With this in mind, the present inventors sought to develop a "collected product" inhibitor by combining an optimised $P_2'$–$P_4'$ fragment with a carboxylate positioned in the same way as the carboxylate in the P-region product inhibitors. They further sought to use the optimised $P_2'$–$P_4'$ fragment (cyclohexylalanine-aspartic acid-leucine-NH$_2$) in the design of small molecular weight inhibitors also having a carboxylate appropriately positioned for binding to the enzyme.

SUMMARY OF THE INVENTION

According to a first aspect of the present invention there is provided a compound of formula (I), or a pharmaceutically acceptable salt or ester thereof:

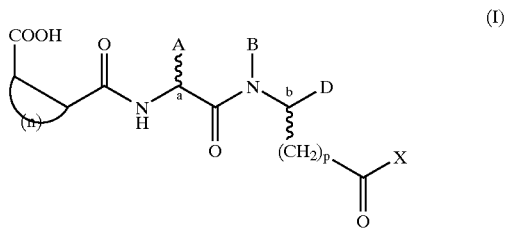

Each of the stereocentres designated "a" and "b" is independently in the R configuration or the S configuration.

Such compounds are suitable for pharmaceutical use and, in particular as inhibitors of HCV NS3 protease. Thus, embodiments of the compound of the above first aspect may be useful in the manufacture of medicaments for the prevention or treatment of hepatitis C virus infection.

In formula (I):

represents a carbocyclic ring and (n) is the total number of carbon atoms in the ring and may be between 4 and 8, but is preferably 5 or 6; the ring may be aromatic or aliphatic;

A is the sidechain of cyclohexylalanine or of an optionally substituted phenylglycine;

B is hydrogen, alkyl of 1–6, preferably 1–2, particularly 1 carbon atom, or is an aralkyl group containing between 7 and 18, preferably from 8 to 14 carbon atoms;

D is hydrogen, or a group of formula:

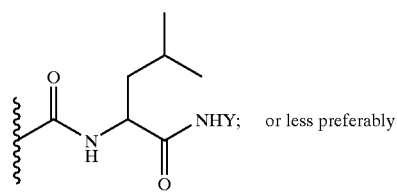

or less preferably

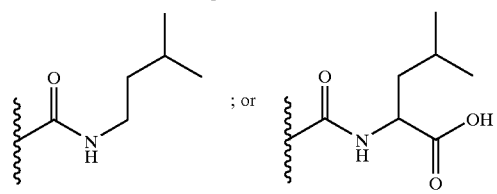

where Y is hydrogen or an alkyl containing 1 to 6 preferably up to 3, especially 2 carbon atoms, or a cycloalkyl group containing 3 to 8 carbon atoms.

p is 1 or 2, preferably 1; and

X is selected from hydroxyl, lower ($C_{1-6}$) alkoxy groups; provided that if B is hydrogen or lower alkyl, D is not also hydrogen, and if D is hydrogen B is an aralkyl group.

An embodiment of the first aspect is a compound of formula (I) wherein

represents a benzene ring or a non-aromatic carbocyclic ring and (n) is the total number of carbon atoms in the carbocyclic ring and is from 4 to 8;

A is (i) cyclohexylmethyl- or (ii) phenyl optionally substituted with from 1 to 3 substituents independently selected from halo, $C_{1-4}$ alkyl, $C_{1-4}$ fluoroalkyl, —O—$C_{1-4}$ alkyl, O—$C_{1-4}$ fluoroalkyl, and $R^a$—C(=O)O—, where $R^a$ is naphthylmethyl-, 2,2-diphenylethyl-, or carboxycyclohexyl-;

B is hydrogen, alkyl of 1–6 carbon atoms or is an aralkyl group containing from 7 to 18 carbon atoms in which the aryl group is optionally substituted with one or more substituents independently selected from halo, $C_{1-4}$ alkyl, $C_{1-4}$ fluoroalkyl, —O—$C_{1-4}$ alkyl, and —O—$C_{1-4}$ fluoroalkyl;

D is hydrogen, or a group of formula:

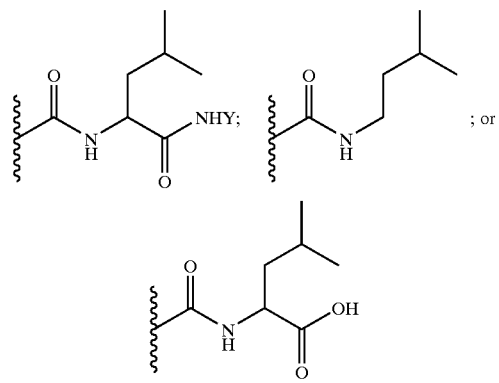

where Y is hydrogen, an alkyl group containing 1 to 6 carbon atoms, or a cycloalkyl group containing 3 to 8 carbon atoms;

each of the stereocentres a and b is independently in the R configuration or the S configuration;

p is 1 or 2; and

X is selected from hydroxyl, and —O—$C_{1-6}$ alkyl groups;

provided that if B is hydrogen or alkyl, D is not also hydrogen, and if D is hydrogen B is an aralkyl group.

As used herein the term "halo" implies a halogen atom selected from fluorine, chlorine, bromine and iodine, preferably fluorine, chlorine or bromine. "Alkyl" encompasses both straight and branched chain groups. The term "fluoroalkyl" likewise implies a straight or branched chain alkyl radical which is substituted by one or more fluorine atoms. "Aralkyl" encompasses straight or branched chain alkyl groups substituted with one or more aromatic groups, provided that the total number of carbon atoms lies in the specified range.

DESCRIPTION OF THE INVENTION

Preferred examples of carbocyclic ring include:

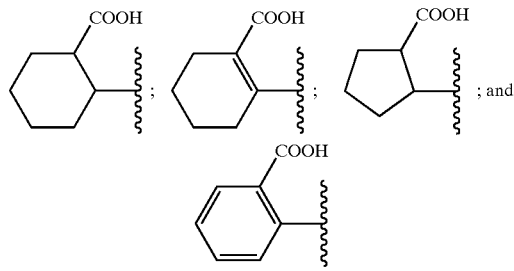

In the case of the cyclohexyl- and cyclopentyl rings it is highly preferred that the substituents are trans to each other. It is further preferred that the stereochemistry in the carbocyclic ring is 1R, 2R.

The stereochemistry at the group A is preferably as shown below; in other words A is preferably the side chain of an L-amino acid:

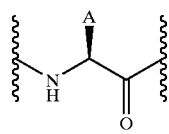

In the case where A is the side chain of phenyl glycine the phenyl ring may be unsubstituted or may be substituted by an optional substituent such as a halogen, preferably fluorine, chlorine or bromine, particularly p-chloro, p-bromo or o-fluoro derivatives, trifluoromethyl (especially p-trifluoromethyl), aralkanoyloxy groups containing from 8 to 20, preferably 12 to 17, especially 12 to 15 carbon atoms and cycloalkanoyloxy groups containing from 5 to 16 carbon atoms, preferably 7 to 12 carbon atoms.

It will be apparent that formula (I) includes two subclasses of compound:
  (i) Compounds having B=hydrogen or lower alkyl and in which D is one of the two possible substituents other than hydrogen set out above;
  (ii) Compounds having D=hydrogen and in which the group B is an aralkyl group.

Each of these subclasses is considered in some more detail below.

Preferred compounds of the first subclass are set out below at formulae (II) and (II'), compounds of formula (II') being less preferred:

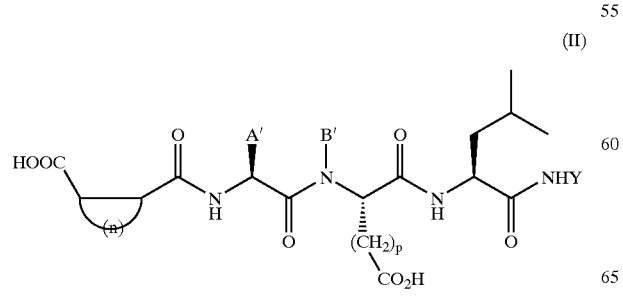

(II)

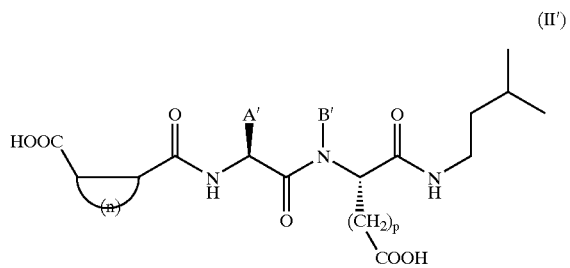

(II')

Although the formulae above show particular, preferred stereochemistry, racemic mixtures and mixtures of diastereomers having the opposite configuration at one or more asymmetric carbon atoms may also be useful.

In these compounds:

p is 1 or 2, but is preferably 1;

preferred carbocyclic rings are as set out above, with trans 1R, 2R cyclohexyl being particularly preferred;

Y is as defined above and is preferably hydrogen, a methyl or ethyl group;

B' is hydrogen or lower alkyl, preferably hydrogen or methyl, especially hydrogen; and A' is the side chain of cyclohexylalanine, phenylglycine, o-fluorophenylglycine and p-chlorophenylglycine. Stated alternatively, A' is cyclohexylmethyl-, phenyl, o-fluorophenyl or p-chlorophenyl.

Examples of compounds in this subclass can be found in the tables infra.

In the second subclass of compounds, when D is hydrogen, B is an aralkyl group, (e.g. an aralkyl group in which the aryl is optionally substituted with from 1 to 3 substituents independently selected from chloro, fluoro, methyl, $CF_3$, $OCH_3$ and $OCF_3$) especially a group of formula:

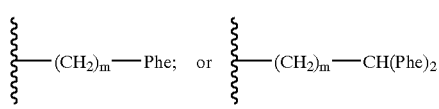

where m is 1 or 2, and Phe is an optionally substituted phenyl group. Suitable optional substituents include halogens, especially chlorine, and lower ($C_{1-6}$, especially $C_1$) alkoxy groups. In one embodiment, Phe is phenyl optionally substituted with from 1 to 3 substituents independently selected from chloro, fluoro, methyl, $CF_3$, $OCH_3$ and $OCF_3$. Particularly preferred examples of the B group include:

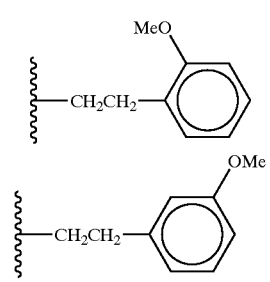

-continued

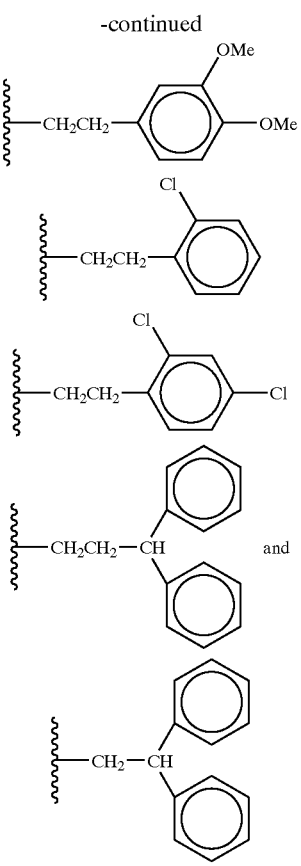

Preferred compounds of this subset include those of formula (III) below:

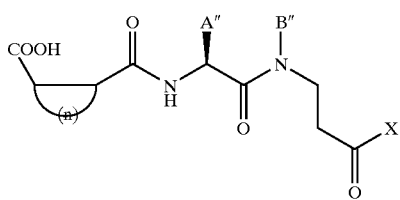

(III)

The preferred stereochemistry at A" is shown; however mixtures including the same compound with the reverse stereochemistry here may also be useful.

Once again, the preferred carbocyclic groups are as set out above with the particularly preferred group being trans 1R, 2R cyclohexyl. B" is one of the preferred aralkyl groups listed above and X is preferably OH.

A" is the side chain of cyclohexylalanine, or of unsubstituted phenylglycine, p-bromophenylglycine, p-trifluromethylphenylglycine or o-fluorophenylglycine. Stated alternatively A" is cyclohexylmethyl-, phenyl, p-bromophenyl, p-trifluoromethylphenyl, or o-fluorophenyl.

Preferred compounds of this subclass are set out in the tables B infra.

Examples of compounds of the present invention may be effective as inhibitors of NS3 protease at micromolar levels.

Preferably, the $IC_{50}$, as measured in the assay described below is less than 100 $\mu$M, particularly less than 50 $\mu$M and, optimally, less than 20 $\mu$M.

According to a second aspect, the present invention provides a compound, salt or ester according to the first aspect, for use in any therapeutic method, preferably for use in inhibiting the HCV NS3 protease, and/or for use in treating or preventing hepatitis C or a related condition. By "related condition" is meant a condition which is or can be caused, directly or indirectly, by the hepatitis C virus, or with which the HCV is in any way associated.

According to a third aspect the present invention provides the use of a compound, salt or ester according to the first aspect in the manufacture of a medicament for the treatment or prevention of hepatitis C or a related condition.

A fourth aspect of the invention provides a pharmaceutical composition which includes one or more compounds, salts or esters according to the first aspect.

The composition may also include a pharmaceutically acceptable adjuvant such as a carrier, buffer, stabiliser or other excipients. It may additionally include other therapeutically active agents, in particular those of use in treating or preventing hepatitis C or related conditions.

The pharmaceutical composition may be in any suitable form, depending on the intended method of administration. It may for example be in the form of a tablet, capsule or liquid for oral administration, or of a solution or suspension for administration parenterally.

According to a fifth aspect of the invention, there is provided a method of inhibiting HCV NS3 protease activity, and/or of treating or preventing hepatitis C or a related condition, the method involving administering to a human or animal (preferably mammalian) subject suffering from the condition a therapeutically or prophylactically effective amount of a composition according to the fourth aspect of the invention, or of a compound, salt or ester according to the first aspect. "Effective amount" means an amount sufficient to cause a benefit to the subject or at least to cause a change in the subject's condition.

The dosage rate at which the compound, salt, ester or composition is administered will depend on the nature of the subject, the nature and severity of the condition, the administration method used, etc. Appropriate values can be selected by the trained medical practitioner. Preferred daily doses of the compounds are likely to be of the order of about 1 to 100 mg, say 0.01 to 2 mg/kg. The compound, salt, ester or composition may be administered alone or in combination with other treatments, either simultaneously or sequentially. It may be administered by any suitable route, including orally, intravenously, cutaneously, subcutaneously, etc. It may be administered directly to a suitable site or in a manner in which it targets a particular site, such as a certain type of cell—suitable targeting methods are already known.

A sixth aspect of the invention provides a method of preparation of a pharmaceutical composition, involving admixing one or more compounds, salts or esters according to the first aspect of the invention with one or more pharmaceutically acceptable adjuvants, and/or with one or more other therapeutically or prophylactically active agents.

In a seventh aspect of the invention a method is provided for synthesizing the compounds of the first aspect. In general, a diacid of formula:

or an activated form thereof, such as the acid anhydride, is condensed with a suitably protected molecule of formula:

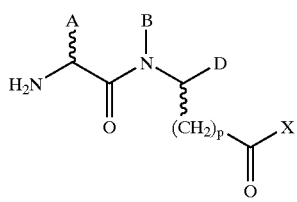

where n, A, B, D, p and X are as defined above. Suitable protecting groups will be apparent to the person of skill in the art and are chosen with a view to preventing reaction of any reactive groups in the groups A, B, D and X with the (activated) diacid or with the $NH_2$ group.

In the case of the first subclass of molecules the peptidic fragment may be synthesized by conventional peptide synthesis using protecting groups well known to peptide chemists. Suitable synthetic procedures include those described in:

"Fmoc Solid Phase Peptide Synthesis, A Practical Approach", W. C. Chan and P. D. White (Eds), Oxford University Press, Oxford (2000); J. Am. Chem. Soc. 114 (1992) 10646–10647 (Zuckerman, R. N. et al); and Tetrahedron Lett., 37 (1996) 5277–5280 (Kolodziej S. A. et al).

Examples of the synthesis of compounds of each subclass are described below. Routine modification of the reaction schemes described could be used to produce other examples of compounds of the invention.

MODES FOR CARRYING OUT THE INVENTION

EXAMPLES

Embodiments of the compounds of the present invention are described below by way of example only.

The following tables I to IV set out exemplary compounds of the invention, together with $IC_{50}$ values for inhibition of HCV NS3 protease as measured by the microplate protease activity assay described subsequently. The configuration of each asymmetric carbon in the exemplified compounds is indicated in the right hand column of each table.

Examples of the synthesis of some of the compounds included in the tables follows the tables.

TABLE I

| Ex. No. | R1 | R2 | IC 50 | Chiral centres |
|---|---|---|---|---|
| 1 | | | 15 uM | R,R,S,S,S |
| 2 | | | 54 uM | S,S,S,S,S |
| 3 | | | 32 uM | R,R,S,S,S |
| 4 | | | 38 uM | S,S,S |
| 5 | | | 60 uM | R,R,S,S,S |
| 6 | | | 64 uM | S,S,S |
| 7 | | | 64 uM | S,S,S |

TABLE II
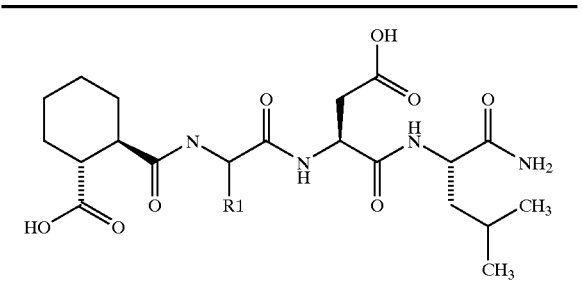
| Ex. No. | R1 | IC 50 | Chiral centres |
|---|---|---|---|
| 8 | one isomer 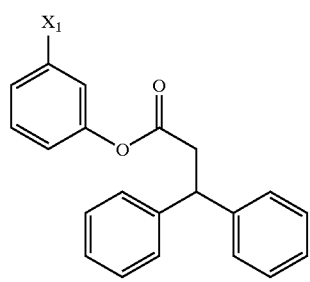 | 13 uM | R,R,[R/S*],S,S *single isomer, not identified |
| 9 | 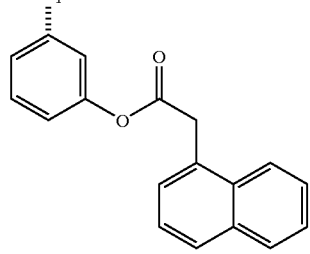 | 22 uM | R,R,S,S,S |
| 10 | 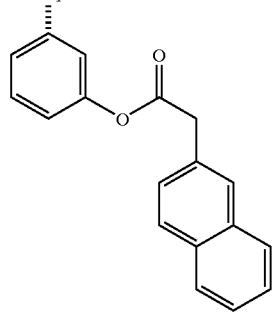 | 22 uM | R,R,S,S,S |
| 11 | 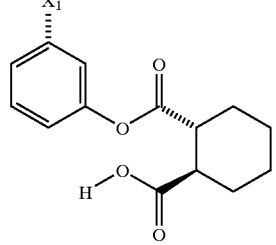 | 35 uM | R,R,S,(R,R),S,S |
TABLE II-continued
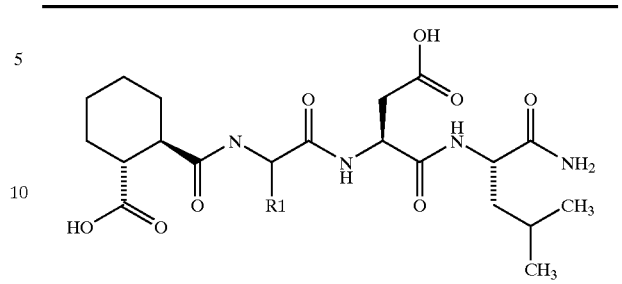
| Ex. No. | R1 | IC 50 | Chiral centres |
|---|---|---|---|
| 12 | 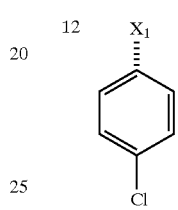 | 37 uM | R,R,S,S,S |
| 13 | 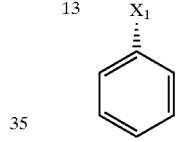 | 40 uM | R,R,S,S,S |
| 14 | 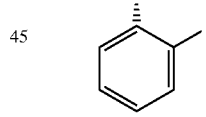 | 47 uM | R,R,S,S,S |
| 15 | 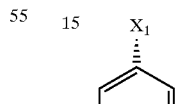 | 26 uM | R,R,S,S,S |

TABLE III

| Ex. No. | | IC 50 | Chiral centres |
|---|---|---|---|
| 16 | | 41 uM | R,R,S,S,S |
| 17 | | 100 uM | R,R,S,S,S |
| 18 | | 115 uM | S,S,S |

TABLE IV

| Ex. No. | | IC 50 | Chiral centres |
|---|---|---|---|
| 19 | | 14 uM | R,R,S |

TABLE IV-continued

| Ex. No. | | IC 50 | Chiral centres |
|---|---|---|---|
| 20 | | 55 uM | R,R,S |
| 21 | | 1.7 uM | R,R,S |
| 22 | | 7 uM | R,R,S |
| 23 | | 6 uM | R,R,S |

TABLE IV-continued
| Ex. No. | | IC 50 | Chiral centres |
|---|---|---|---|
| 24 | 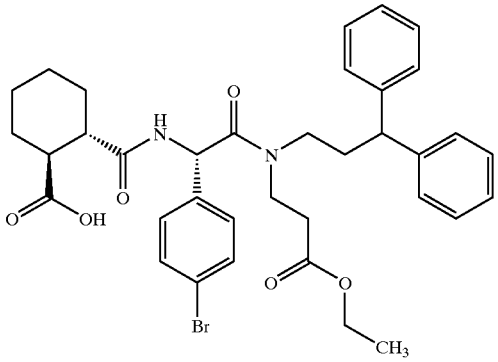 | 60 μM | R,R,S |
| 25 | 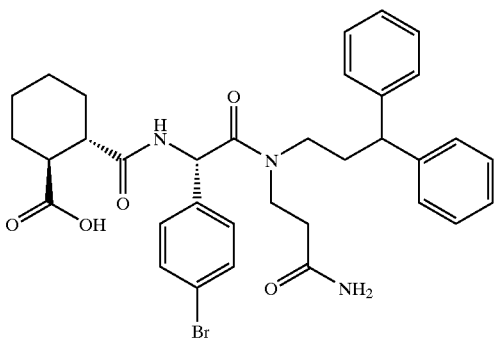 | 59 μM | R,R,S |
| 26 | 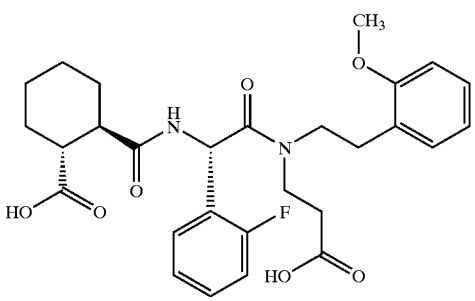 | 44 uM | R,R,S |
| 27 | 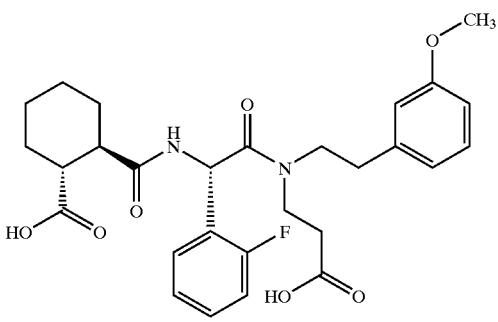 | 66 uM | R,R,S |

TABLE IV-continued

| Ex. No. | | IC 50 | Chiral centres |
|---|---|---|---|
| 28 | | 70 uM | R,R,S |
| 29 | | 39 uM | R,R,S |
| 30 | | 49 uM | R,R,S |
| 31 | | 123 uM | R,R,S |

TABLE IV-continued

| Ex. No. | | IC 50 | Chiral centres |
|---|---|---|---|
| 32 | | 133 uM | R,R,S |
| 33 | | 177 uM | R,R,S |

Synthetic Examples

General Methods.

Unless indicated otherwise, all the materials were obtained from commercial suppliers and used without further purification. Thin layer chromatography (TLC) was performed in silica gel 60 $F_{254}$ precoated plates (Merck). Analytical HPLC was performed on a Beckman System Gold chromatograph equipped with a diode-array detector (dual wavelength monitoring, 214 and 254 nm) and a Beckmann C-18 column (250×4.6 mm, 5 μm), operating flow rate 1 mL min$^{-1}$. Preparative HPLC was performed on a Waters 600E chromatograph equipped with a Jasco UV-975 detector (monitoring wavelength, 254 nm and 214 nm), Waters Delta-Pak™ C-18 column (100×250 mm, 15 μm). The operating flow rate was 30 mL min$^{-1}$. The solvent system was: eluent A, water (0.1% TFA); eluent B, MeCN (0.1% TFA). NMR spectra were recorded on a Brucker instrument operating at 400 MHz ($^1$H). Chemical shifts are reported in ppm relative to the solvent residual signal.

Unless indicated otherwise, the amino acids in the examples below are always in the L-configuration.

Example A:

Synthesis of R$_1$R-cyclohexane-1,2-dicarboxylate monoamide of Cha-Asp-Leu-NH$_2$(Tab. I ex. No 1) and SS-cyclohexane-1,2-dicarboxylate monoamide of Cha-Asp-Leu-NH$_2$(Tab. I ex. No 2).

Trans-D,L-cyclohexane-1,2-dicarboxylate monoamide of Cha-Asp-Leu-NH$_2$ was prepared according to Scheme 1.

Manual Solid phase peptide synthesis was performed on 200 mg of NovaSyn TGR® resin (0.24 mmol/g, 0.048 mmol) using a 5-fold excess (over the resin amino groups) of amino acid/PyBOP/HOBt/DIEA (5:5:5:10), or 5-fold excess of trans-1,2-cyclohexanedicarboxylic anhydride.

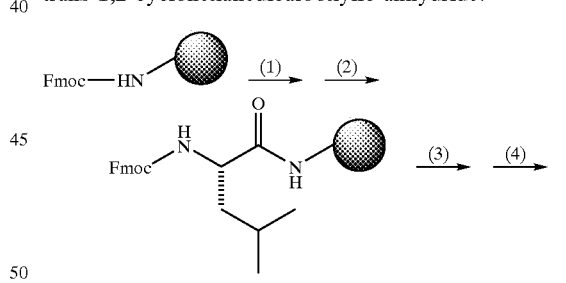

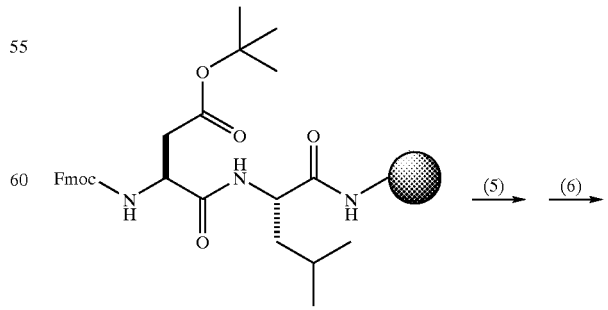

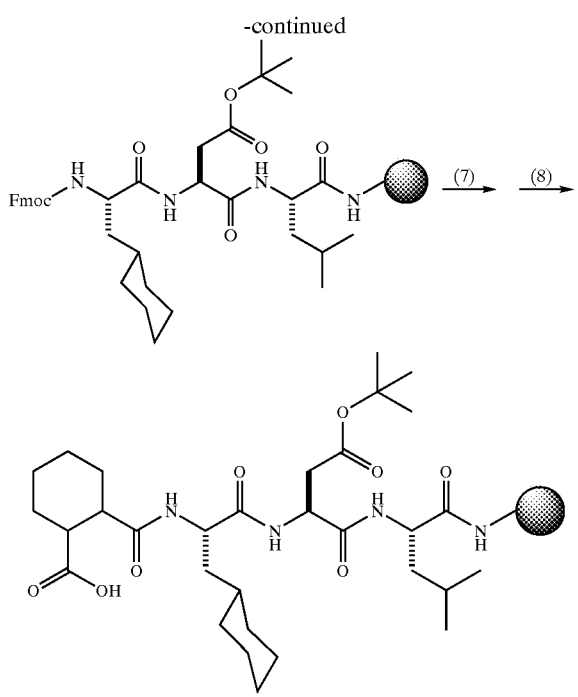

Scheme 1. (1), (3), (5) and (7): 1.5 ml of 20% piperidine/DMF, 20 min, 25° C., followed by DMF washes (5×2 ml); (2): 85 mg of Fmoc-Leu-OH (0.24 mmol), 125 mg of PyBOP (0.24 mmol), 37 mg of HOBt (0.24 mmol) and 82 µl of DIEA (0.48 mmol) dissolved in 200 µl of DMF. Coupling time: 30 min, followed by DMF washes (5×2 ml); (4): as in (2), but 99 mg of Fmoc-Asp(OtBu)-OH (0.24 mmol) instead of Fmoc-Leu-OH; (6): as in (2), but 94 mg of Fmoc-Cha-OH (0.24 mmol) instead of Fmoc-Leu-OH; (8): 37 mg of trans-1,2-cyclohexanedicarboxylic anhydride (0.24 mmol) dissolved in 200 µl of DMF. Coupling time: 30 min, followed by DMF washes (5×2 ml).

At the end of the assembly, the resin was washed with DMF, Methanol, and DCM and dried to constant weight in vacuo. The compound was simultaneously cleaved from the resin and side-chain deprotected by treatment of the dry resin with 1.5 ml of TFA/H$_2$O 90/10 for 1 h. The TFA solution was filtered from the resin and concentrated in vacuo. 1.5 ml of cold diethylether was added (bringing about visible precipitation) and the solvent was evaporated; this operation was repeated twice. After a last addition of cold diethylether, the suspension was centrifuged, the ether removed and the solid dried in vacuo. The compound was obtained as a mixture of two diastereoisomers. Yield: 15 mg (56.6%).

Analytical HPLC of the product was performed using isocratic elution at 30% B for 5 min, followed by a linear gradient 30%–70% B over 20 min. The two peaks eluted at $t_R$=13.7' and $t_R$=19.0' corresponded to the expected diastereoisomers.

Preparative HPLC was performed as follows: the crude sample (15 mg) was dissolved in 0.5 ml of DMSO, diluted to 7 ml with H$_2$O/CH$_3$CN, and loaded onto the preparative column at a flow rate of 5 ml/min. The flow was then raised to 30 ml/min and the preparative run started with an isocratic step (30% B, 5 min) followed by a linear gradient 30%–60% B over 20 min. The first eluted species was named "isomer A" while the second one was named "isomer B". Both were lyophilized.

Isomer A (Tab. I Ex. No 1). Analytical HPLC: linear gradient 35%–65% B over 20 min, $t_R$=7.64', purity>99%;

Isomer B (Tab. I ex. No 2): Analytical HPLC: linear gradient 35%–65% B over 20 min, $t_R$=13.05', purity>99%;

The other analytical data were identical for the two isomers.

Ion-spray mass spectrometry: molecular weight=552.5 Da (expected M.W. 552.67 Da). $^1$HNMR (400.13 MHz, DMSO, 300K): δ 8.00 (d, 1H), 7.93 (d, 1H), 7.65 (d, 1H), 7.05 (d, 2H), 4.45 (multiplet, 1H), 4.16 (multiplet, 2H), 2.72–2.68 (dd, 1H), 2.57 (d, 1H), 2.45–2.35 (broad multiplet, 2H), 1.95–1.84 (broad multiplet, 2H), 1.76–1.00 (series of multiplets, 22H), 0.87 (d, 3H), 0.77 (d, 3H).

Assignment of the absolute configuration of Isomers A and B. In order to assign the absolute configuration of the two chiral carbons at the trans-carboxycyclohexanecarbonyl moiety of the two diastereoisomers (Tab. I ex. No 1 and No 2), the synthesis was repeated using the (1R,2R)-cyclohexanedicarboxylic acid to obtain the corresponding isomer in the final product. The synthetic scheme was as previously described (Scheme 1) with the exception of step (8):

41 mg of (1R,2R)-cyclohexanedicarboxylic acid (0.24 mmol), 125 mg of PyBOP (0.24 mmol), 37 mg of HOBt (0.24 mmol) and 82 µl of DIEA (0.48 mmol) dissolved in 200 µl of DMF. Coupling time: 30 min, followed by DMF washes (5×2 ml). The work-up and cleavage were also performed as previously described. Analytical HPLC of the crude product in the same conditions used for the diastereoisomeric mixture showed a single peak with a $t_R$=7.62' corresponding to the retention time of the isomer A (Tab. I ex. No 1). Co-injection with purified isomer A revealed a single peak with $t_R$=7.59'. Therefore the assignment of the stereochemistry for the previously synthesized isomers Isomer A

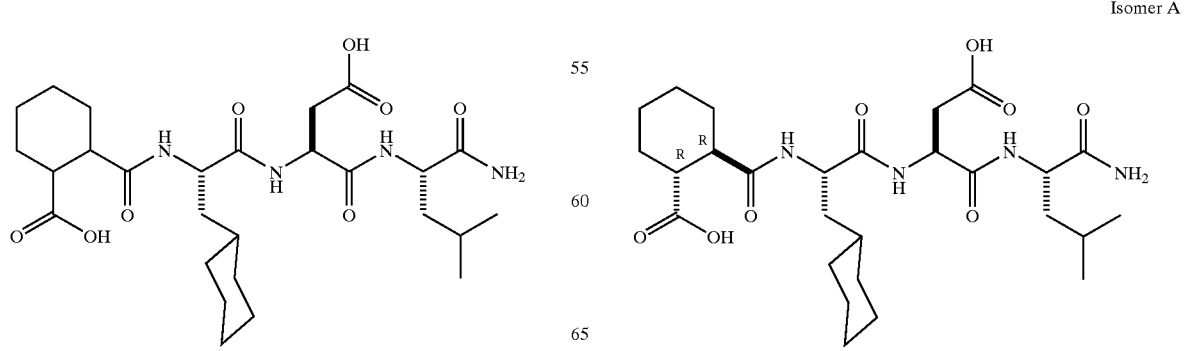

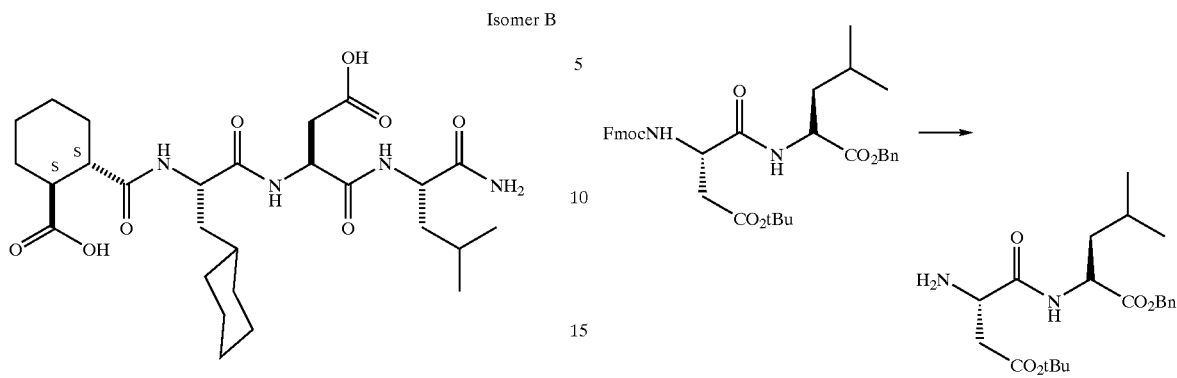

Example B

Synthesis of Trans-D,L-cyclohexane-1,2-dicarboxylate monoamide of Cha-Asp-Leu-NHEt; R,R-cyclohexane-1,2-dicarboxylate monoamide of Cha-Asp-Leu-NHEt; and S,S-cyclohexane-1,2-dicarboxylate monoamide of Cha-Asp-Leu-NHEt (Tab. I ex. No 3).

Step 1: Synthesis of Fmoc-Asp-(OtBu)-Leu-OBn.

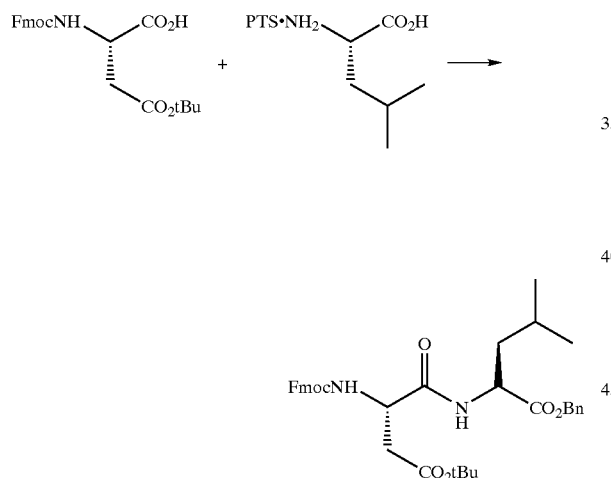

Fmoc-Asp(OtBu)-OH (5.00 gr, 12.15 mmol) was dissolved in 200 mL DCM. EDCA (2.33 gr, 12.15 mmol), HOBT (6.32 gr, 12.15 mmol), H-Leu-OBn PTS salt (4.78 gr, 12.15 mmol) and DIPEA (2.11 mL, 12.15 mmol) were added in the order while stirring.

After 12 hrs the solution was washed with 1N HCl (3×100 mL), 5% $Na_2CO_3$ (3×100 mL) and brine, then dried ($Na_2SO_4$) and concentrated to yield 7.60 gr of a white foam (98%).

$^1$H-NMR (CDCl$_3$) δ 7.80(d, 2H), 7.60(d, 1H), 7.50–7.30 (m, 10H), 7.00(d, NH), 6.00(d, NH), 5.20(m, 2H), 4.62(m, 2H), 4.41(d, 2H), 4.24(dd, 1H), 2.93(dd, 1H), 2.58(dd, 1H), 1.70–1.55(m, 3H), 1.45(s, 9H), 0.93(s, 9H).

Step 2: Synthesis of H-AsP(OtBi)-LeuOBn.

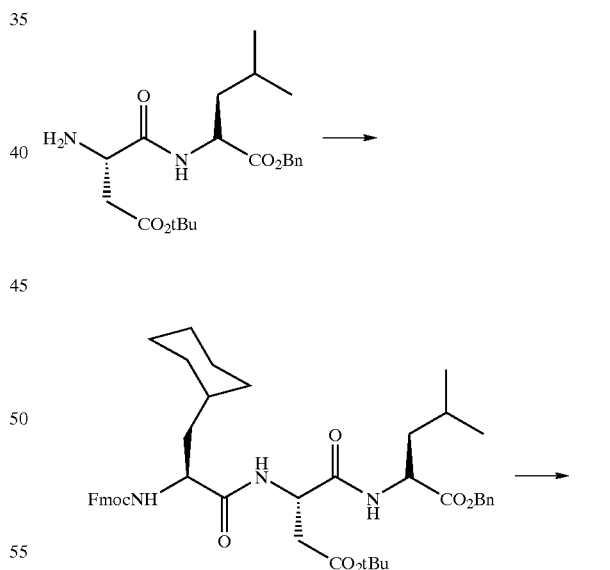

Fmoc-Asp(OtBu)-Leu-OBn (1.00 gr, 1.60 mmol) was dissolved in 25 mL DCM. 4-aminomethylpiperidine (1 mL, 8.0 mmol) was added and stirring was continued at room temperature. At the end of the reaction (TLC control, silica, EtOAc/dichloromethane 1:4) the solution was washed with water (3×5 mL) and brine, dried over $Na_2SO_4$ and filtered. The resulting solution was directly poured onto a chromatographic column previously equilibrated with DCM. Chromatographic purification (eluent DCM, then dichloromethane/EtOAc 4:1) yielded 606 mg of product (97%) as a colourless oil.

$^1$H-NMR (CDCl$_3$) δ 7.71(d, 1H), 7.35(m, 5H), 5.10(m, 10H), 7.00(d, NH), 6.00(d, NH), 5.20(m, 2H), 4.62(m, 2H), 4.41(d, 2H), 4.24(s, 2H), 4.60(m, 1H), 3.65(dd, 1H), 2.80 (dd, 1H), 1.70–1.50(m, 3H), 1.40(s, 9H), 0.90(m, 6H).

Step 3: Synthesis of Fmoc-Cha-Asp(OtBu)-Leu-OBn.

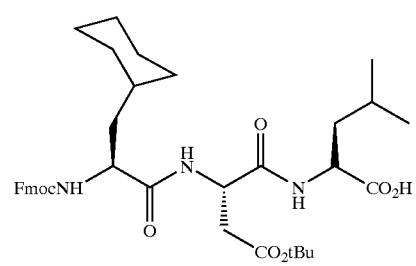

H-Asp(OtBu)-Leu-OBn (606 mg, 1.54 mmol) was dissolved in DCM (10 mL) and Fmoc-Cha-OH (610 mg, 1.54 mmol), EDCA (330 mg, 1.69 mmol) and HOBT (1.2 gr, 2.31 mmol) were added. The resulting mixture was stirred at room temperature for 12 h. The solution was diluted with EtOAc (150 mL), washed with 1N HCl (3×100 mL), 5% $Na_2CO_3$ (3×50 mL) and brine then dried ($Na_2SO_4$) and concentrated to obtain 1.10 gr of a white solid (99%), which was used without further purification in the next step.

Fmoc-Cha-Asp(OtBu)-Leu-OBn (1.10 gr, 1.54 mmol) was dissolved in MeOH (10 mL), 50 mg of 5% Pd/C were added and the resulting misture was stirred for 6 h under $H_2$ atmosphere. After filtration and distillation of the solvents in vacuo, 803 mg of a white foam were obtained (77%).

$^1$H-NMR (CDCl$_3$) δ 7.80 (d, 2H), 7.60(m, 2H), 5.10(m, 10H), 7.42(m, 3H), 7.31(m, 2H), 7.20(d, 1H), 5.20(d, 1H), 4.80(m, 1H), 4.40–4.34(m, 3H), 4.21(m, 2), 2.90(dd, 1H), 2.60(dd, 1H), 1.84–1.350(m, 14H), 1.40(s, 9H), 0.90(m, 6H).

Step 4: Synthesis of Fmoc-Cha-AsP (OtBu)-Leu-NHEt.

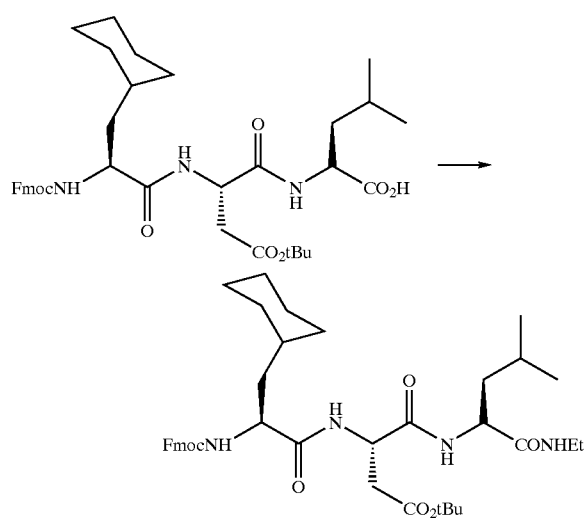

A solution of

Fmoc-Cha-Asp(OtBu)-LeuOH (803 mg, 1.19 mmol), EDCA (341 mg, 1.77 mmol) and HOBT (115 mg, 1.77 mmol) in DCM (20 mL) was stirred at room temperature. A solution of ethylamine hydrochloride (145 mg, 1.77 mmol) and DIPEA (0.31 mL, 1.77 mmol) in DCM (20 mL) was added dropwise. After 5 h the solution was diluted with 50 mL DCM, washed with 1N HCl (3×25 mL), 5% $Na_2CO_3$ (3×50 mL) and brine, then dried ($Na_2SO_4$) and concentrated to yield 1.00 g of a white solid which was used without further purification in the next step.

$^1$H-NMR. (CDCl$_3$) δ 7.80(d, 1H), 7.60(m, 3H), 7.4-(m, 2H), 7.31 (m, 2H), 7.00(d, 1H), 6.55(dd, 1H), 5.20(d, 1H), 4.60(m, 1H), 4.50–4.40(m, 3H), 4.30(m, 1H), 4.40(m, 1H), 3.30(m, 2H), 2.90(dd, 1H), 2.35(dd, 1H), 1.80–1.20(m, 12H), 1.35(s, 9H), 1.13(t, 3H), 0.90(m, 4H), 0.80(m, 6H).

Step 5: Synthesis of H-Cha-Asp(OtBu)-Leu-NHEt.

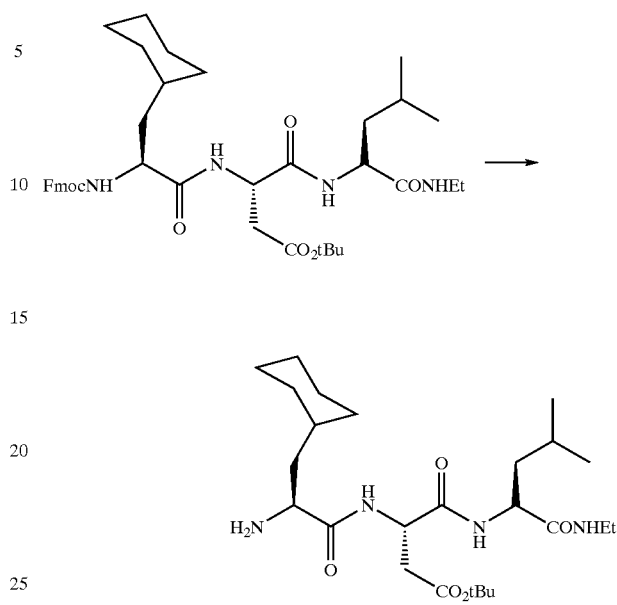

Fmoc-Cha-Asp(OtBu)-Leu-NHEt (1.06 gr, 1.19 mmol) was dissolved in 10 mL DCM. 4-aminomethylpiperidine (1 mL, 8.0 mmol) was added and stirring was continued at room temperature. At the end of the reaction (TLC control, silica, EtOAc/DCM 1:4) the solution was washed with water (3×5 mL) and brine, dried over $Na_2SO_4$ and filtered. The resulting solution was directly poured on a chromatographic column previously equilibrated with DCM. Chromatographic purification (eluent DCM, then DCM/EtOAc 4:1) yielded 308 mg of product (55%).

$^1$H-NMR (CDCl$_3$) δ 8.20(d, 1H), 6.60(d, 1H), 6.45(dm, 1H), 4.68(m, 1H), 4.40(m, 1H), 3.44(dd, 1H), 3.26(m, 2H), 2.80(m, 2H), 1.40–1.16(m, 14H), 1.45(s, 9H), 1.13(t, 3H), 1.00(m, 2H), 0.9(m, 6H).

Step 6: Synthesis of Trans-D,L-cyclohexane-1,2-dicarboxylate monoamide of Cha-Asp-Leu-NHEt.

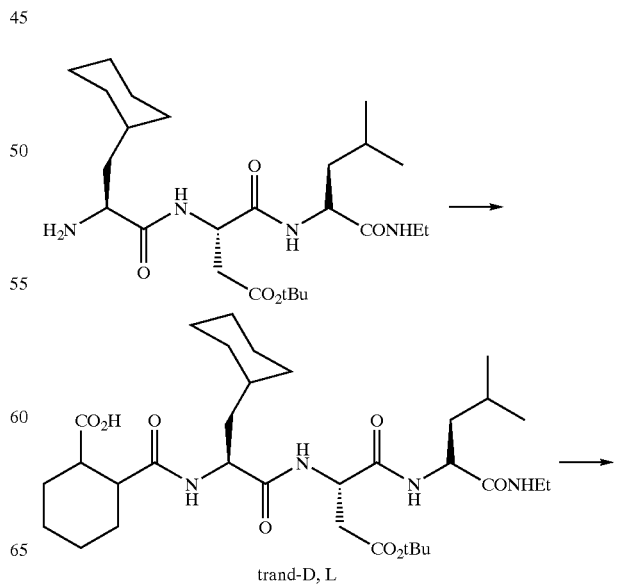

trand-D, L

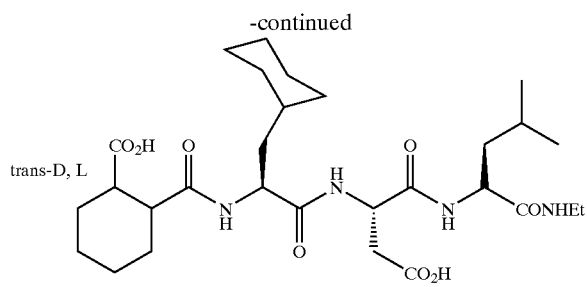

A solution of H-Cha-Asp(OtBu-Leu-NHEt (100 mg, 0.21 mmol), DMAP (cat. amount) and trans-(D,L)-cyclohexanedicarboxylic anhydride in DCM (5 mL) was stirred at room temperature for 3 h. Then the solution was diluted with DCM (20 mL), washed with 1N HCl (2×10 mL) and brine, then dried and concentrated to obtain 98 mg (73%) of a white solid.

The solid was dissolved in water (1 mL) and TFA (4 mL) and was stirred at room temperature for 1 h. Solvents were then distilled off in vacuo. Trituration of the residual oil with diethyl ether yielded 60 mg of a white solid.

$^1$H-NMR (DMSO-6d) δ 8.20, 8.00, 7.90, 7.85, 7.65, 7.60, 7.50 (NHs, 4H), 4.45(m, 1H), 4.14(m, 2H), 3.00(dd, 2H), 2.70(m, 1H), 2.50(m, 1H), 2.41(m, 2H), 2.05–1.05(m, 22H), 1.00(t, 3H), 0.80(dd, 6H), 0.80(m, 2H).

The two distereoisomers were separated by preparative HPLC (linear gradient 30%–90% B in 25 min) to obtain:

R, R-cyclohexane-1,2-dicarboxylate monoamide of Cha-Asp-Leu-NHEt retention time 10 min.

S,S-cyclohexane-1,2-dicarboxylate monoamide of Cha-Asp-Leu-NHEt (Tab. I, Example No 3): retention time 20 min.

Example C

Synthesis of Compound (Tab. IV Ex. No 19) and its Stereoisomer

Solid phase synthesis was performed on 100 mg of Wang resin (Novabiochem, 0.96 mmol/g, 0.096 mmol). The compound was prepared according to the following scheme:

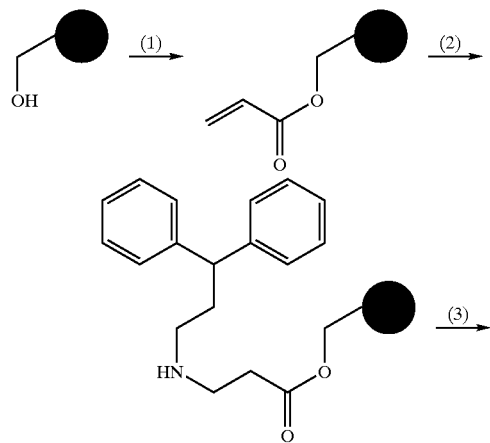

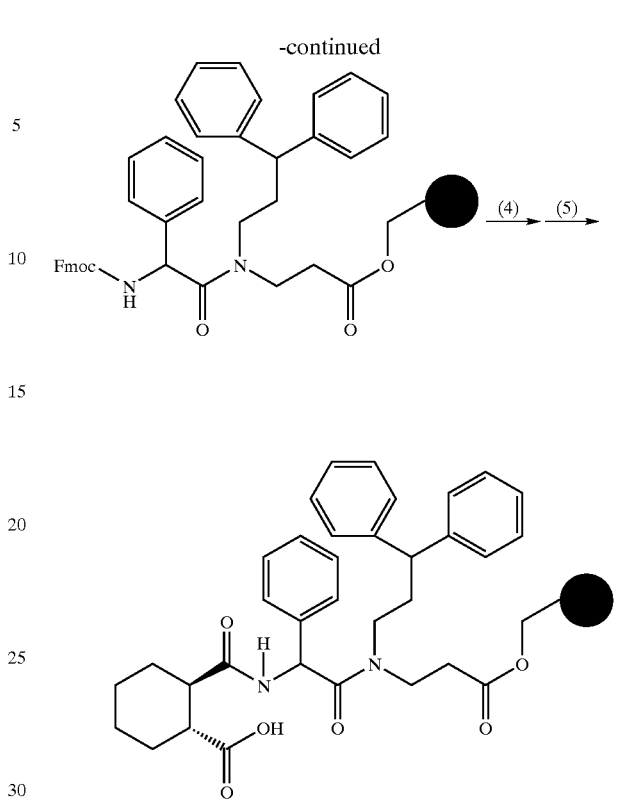

Scheme 2.: (1): 76.4 μl TEA (0.53 mmol), then 38.2 μl ACC (0.48 mmol), were added to the resin pre-swollen in 600 μl of DCM. Reaction time: 2h, followed by DCM washes (5×2 ml). The procedure was repeated with a lower excess of reagents: 46 ul of TEA (0.32 mmol), then 23 μl of ACC (0.29 mmol), were added to the resin swollen in 600 μl of DCM. Reaction time: 2 h. The resin was sequentially washed with DCM, DMF and MeOH. (2): 184 μl of 3,3-diphenylpropylamine (0.96 mmol) dissolved in 776 μL DMSO (1 M solution). Reaction time: 22 h, room temperature, with stirring. The resin was washed with DMSO, MeOH and DCM. (3): 143 mg Fmoc-Phg-OH (0.38 mmol), 146 mg HATU (0.38 mmol) and 131 μl DIEA (0.38 mmol) dissolved in 400 μl of DMF. Coupling time: 2 h, followed by DMF washes (5×2 ml). Partial racemization of the Phg occurs in these conditions. (4): 1.5 ml of 20% piperidine/DMF, 20 min, followed by DMF washes (5×2 ml). (5): 81 mg of 1R, 2R)-cyclohexanedicarboxylic acid (0.48 mmol), 250 mg PyBOP (0.48 mmol), 71 mg HOBt (0.48 mmol) and 164 μl DIEA (0.96 mmol) dissolved in 400 μl DMF. Coupling time: 1 h, followed by DMF washes (5×2 ml).

At the end of assembly, the resin was washed with DMF, MeOH, and DCM and dried to constant weight in vacuo. The compound was cleaved from the resin by treatment with 3 ml of TFA/H$_2$O 95/5 for 20 min. The TFA solution was filtered from the resin which was washed with DCM (3×1 ml). The TFA/DCM solution was concentrated in vacuo. 3 ml of cold diethylether were added (inducing formation of a fine precipitate) and the solvent evaporated; this operation was repeated once again, then the sample was lyophilized. The compound was obtained as a mixture of diastereoisomers (yield, 39 mg, 71%):

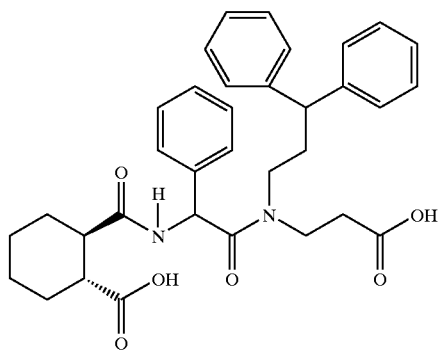

Analytical HPLC of the product was performed using a linear gradient 30%–80% B over 15 min. The two peaks eluting at $t_R$=12.5' and $t_R$=14.0' corresponded to the two expected diastereoisomers. Preparative HPLC was performed as follows: the crude sample (10 mg) was dissolved in 1 ml of DMSO, diluted to 5 ml with $H_2O/CH_3CN$, and loaded onto the preparative column at a flow rate of 5 m/min. The flow was then raised to 30 ml/min and the preparative run started with an isocratic step (40% B, 5 min) followed by a linear gradient 40%–80% B over 20 min. The first eluted species was named "isomer A" while the second one was named "isomer B". Both were 15 lyophilized.

Isomer A (Tab. IV Ex. No 19). Analytical HPLC: linear gradient 30%–80% B over 15 min, $t_R$=12.59', purity>99%;

Isomer B: Analytical HPLC: linear gradient 30%–80% B over 15 min, $t_R$=14.08', purity>99%;

The other analytical data were identical for both compounds.

Ion-spray mass spectrometry: molecular weight=570.5 Da 20 (expected M.W. 570.69 Da). $^1$HNMR (400.13 MHz, DMSO, 300K): δ 8.45–8.15 (dd, 1H), 7.43–7.10 (m, 15H), 6.93–6.83 (m, 1H), 5.80–5.40 (dm, 1H), 4.05–2.95 (series of multiplet, 6H), 2.43–2.10 (series of multiplet, 4H), 2.00–1.82 (broad m, 2H), 1.78–1.60 (broad m, 2H), 1.32–1.10 (broad m, 4H).

By analogy with the previously synthesized analogous compounds, in which the R configuration corresponded to the species with the lower retention time, the S configuration at the Phg was tentatively assigned to isomer A, and the R configuration to isomer B:

Isomer A

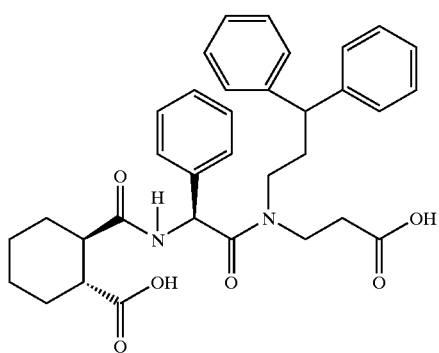

Isomer B

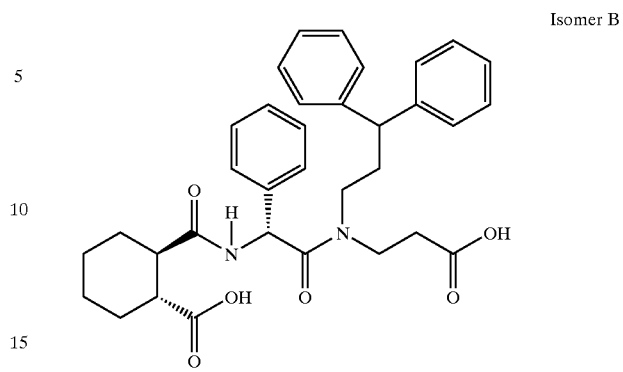

Example D

Synthesis of Compound (Tab. IV Ex. No 21) and its Stereoisomer

Step 1: Synthesis of N-3,3-diphenylpropyl-β-alanine-OtBu.

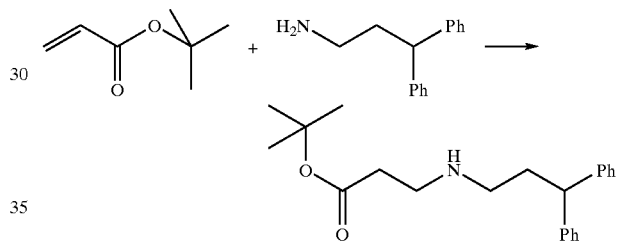

3,3-diphenylpropylamine (2.00 gr, 9.76 mol) and t-butylacrylate (1.28 gr, 9.76 mmol) in EtOH (5 mL) were stirred at room temperature for 12 h; the solvents were then distilled off in vacuo. Chromatographic purification of the residue (silica, DCM/EtOAc 1:1 then DCM/EtOAc 1:1, 1% TEA) yielded 2.61 gr of product (79%) as a colourless oil.

$^1$H-NMR (DMSO-$^6$d) δ 7.25(m, 10H), 2.6(m, 1H), 6.45 (dm, 1H), 4.68(m, 1H), 4.40(m, 1H), 3.44(dd, 1H), 3.26(m, 2H), 2.80(m, 2H), 2.3(m, 2H), 2.20(m, 2H), 2.05(m, 2H), 1.30(s, 9H).

Step 2: Synthesis of 4-bromo-D,L-phenyl glycine ester of N-3,3-diphenylpropyl-β-alanine-OtBu.

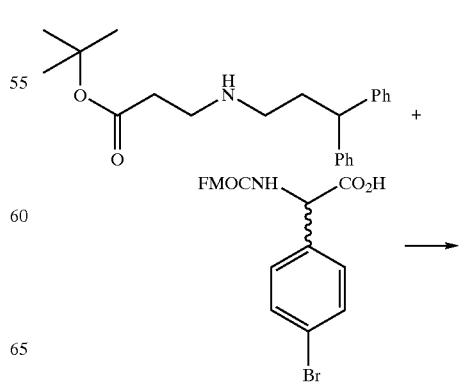

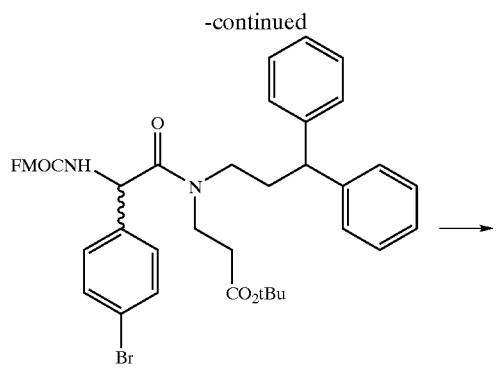

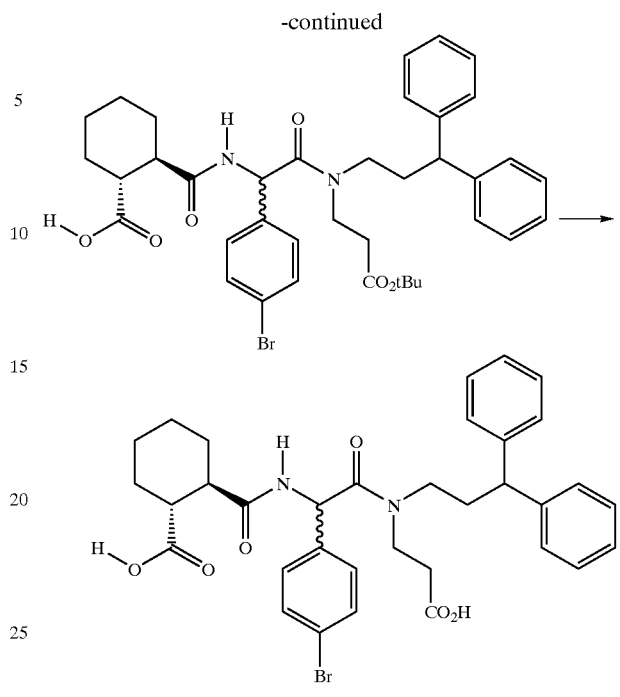

Fmoc-4-bromo-D,L-phenyglycine (161 mg, 0.36 mmol) was dissolved in 10 mL (1:1) DCM/DMF. HATU (163 mg, 0.43 mmol), DIPEA (0.14 mL, 0.78 mmol) and N-3,3-diphenylpropyl-β-alanine-OtBu (133 mg, 0.39 mmol) were added in that order. Stirring was continued at room temperature for 12 h. The mixture was then diluted with DCM (30 mL), washed with 1N HCl (3×10 mL), 10% Na$_2$CO$_3$ (2×10 mL) and brine, then dried (Na$_2$SO$_4$) and concentrated in vacuo to yield 314 mg of product as a yellow oil. This was used in the next step without further purification. The oil was dissolved in 15 mL DCM and 0.45 mL of 4-aminomethylpiperidine (3.57 mmol) were added. At the end of the reaction (TLC control, DCM/MeOH 9:1) the solution was diluted with 30 mL DCM, washed with water (2×10 mL) and brine, dried over Na$_2$SO$_4$ and filtered. The resulting solution was directly poured onto a chromatographic column previously equilibrated with DCM. Chromatographic purification (eluent DCM, then DCM/MeOH 9:1) yielded 101 mg of a colourless oil (combined yield for the two steps, 51%).

Step 3: Synthesis of R,R-cyclohexane dicarboxylic acid monoamide of (D,L)-p-Br-phenylglycinamide of N-3,3-diphenylpropyl-N-2-carboxyethylamide.

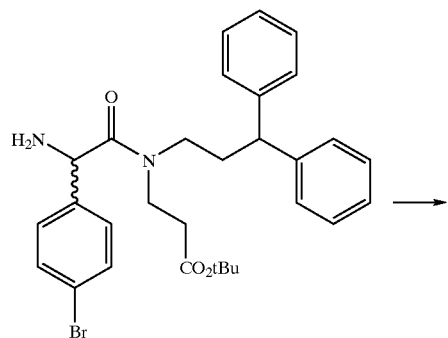

A solution of 4-bromo-D,L-phenyl glycine ester of N-3,3-diphenylpropyl-b-alanine-OtBu (101 mg, 0.18 mmol), R,R-cyclohexanedicarboxylic acid (33 mg, 0.19 mmol), EDCA (35 mg, 0.18 mmol) and DMAP (22 mg, 0.18 mmol) in 5 mL DCM was stirred at room temperature for 12 h. Then it was diluted with DCM (10 mL), washed with 1 N HCl (3×5 mL) and brine, dried and concentrated to yield 135 mg of product as a white foam. The foam was dissolved in 10 mL (95:5) TFA/H$_2$O and stirred for 1 h at room temperature. The solvents were then distilled off in vacuo. The two distereoisomers were separated by preparative HPLC (linear gradient 30%–90% B in 25 min) to obtain:

Example 21 (Tab IV) (R,R,S isomer), retention time 13 min, 30 mg $^1$H-NMR (DMSO-d$_6$) δ 8.45 and 8.35 (d, 1H, NH); 7.50–6.70 (m, 14H); 5.80 and 5.45 (d, 1H), 4.00–3.15 (m, 4H), 3.05 (m, 2H), 2.50–2.00 (m, 6H), 2.00–1.10 (m 4H).

(R,R,R isomer), retention time 15 min, 35 mg $^1$H-NMR (DMSO-d$_6$) δ 8.45 and 8.20 (d, 1H, NH); 7.50–6.80 (m, 14H); 5.85 and 5.45 (d, 1H), 3.80–2.80 (m, 6H), 2.50–2.00 (m, 6H), 2.00–1.10 (m 4H).

Microplate Protease Activity Assay

The HCV-protease (J strain) was stored until use at −80° C. in 250 mM NaCl, phosphate buffer pH 6.5, 50% glycerol, 0.1% CHAPS. As protease co-factor the peptide Pep4AK (KKKGSVVIVGRIILSGR-NH$_2$), spanning the central hydrophobic core (residues 21–34) of the NS4A protein, with a three-lysine tag at the N-terminus to increase solubility (Bianchi, E. et al., *Biochemistry* 36, 7890–7897;1997), was used. Pep4AK was stored at −80° C. in DMSO; the tritiated substrate Ac-DEMEECASHLPYK ($^3$H-Ac)-NH$_2$, and the corresponding cold substrate Ac-DEMEE-CASHLPYK(Ac)-NH$_2$ were stored at −80° C. in DMSO/DTT.

The assay was run in Costar polypropylene 96-well plates. The composition of the reaction mixture was as follows (100 μl):

Glycerol 15%
DTT 30 mM
Hepes pH 7,5 50 mM
Triton X-100 0.05%
Protease 10 nM
hot+cold substrate 5 μM (300.000 cpm)
Pep4AK 15 μM Test compounds were dissolved—in DMSO (final concentration 10% DMSO)

Pep4AK was pre-incubated with protease for 5 min prior to addition of substrate mix. In these conditions, the substrate Km was 7±2 μM. Test compounds were added at 8 different concentrations in 8 different wells. Plates were shaken for 30 minutes at room temperature, then an ionic exchange resin (100 μl of 20% Fractogel TSK-DEAE® 650S, Merck) was added to capture unprocessed substrate and plates shaken for another 10 minutes. After allowing the resin to settle by centrifugation, 30 μl of the reaction mix were transferred in a 96-well plate (Picoplate, Packard), admixed with 250 μl of scintillation cocktail Microscint 40, and the radioactivity measured in a scintillation Packard Top Count β-counter.

$IC_{50}$ was calculated from the test compound dilution curve, as the concentration of compound giving 50% inhibitions.

Abbreviations and Symbols Used in the Text
ACC, acryloyl chloride;
Cha, cyclohexylalanine;
CHAPS, 3-[(3-colamidopropyl)-dimethyl-ammonium]-1-propan-sulfonate;
DCM, dichloromethane;
DIEA, diisopropylethylamine;
DMF, N,N'-dimethylformamide;
DMSO, dimethyl sulfoxide;
DTT=Ditiotreithol
EDCA, ethyl-diisopropylcarbodiimide;
Fmoc, 9-fluorenylmethyloxycarbonyl;
HATU, [O-(7-azabenzotriazol-1-yl)-1,1,3,3-tetramethyluronium hexafluorophosphate];
HOBt, N-hydroxybenzotriazole;
Phg, phenylglycine;
PTS, p-toluensulphonate;
PyBOP, (benzotriazol-1-yloxy)tris(pyrrolidino)phosphonium hexafluorophosphate;
tBu, tert-butyl;
TEA, triethylamine;
TFA, trifluoroacetic acid.

What is claimed is:

1. A compound of formula (I), or a pharmaceutically acceptable salt or ester thereof:

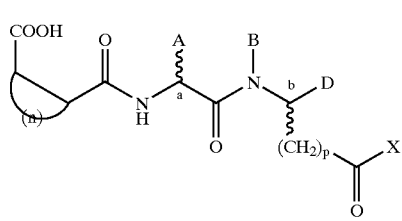

(I)

wherein:
represents a benzene ring or a non-aromatic carbocyclic ring and (n) is the total number of carbon atoms in the carbocyclic ring and is from 4 to 8;

A is (i) cyclohexylmethyl- or (ii) phenyl optionally substituted with from 1 to 3 substituents independently selected from halo, $C_{1-4}$ alkyl, $C_{1-4}$ fluoroalkyl, —O—$C_{1-4}$ alkyl, O—$C_{1-4}$ fluoroalkyl, and $R^a$—C(=O)O—, where $R^a$ is naphthylmethyl-, 2,2-diphenylmethyl-, or carboxycyclohexyl-;

B is hydrogen, lower alkyl of 1–6 carbon atoms or is an aralkyl group containing from 7 to 18 carbon atoms in which the aryl group is optionally substituted with one or more substituents independently selected from halo, $C_{1-4}$ alkyl, $C_{1-4}$ fluoroalkyl, —O—$C_{1-4}$ alkyl, —O—$C_{1-4}$ fluoroalkyl;

D is hydrogen, or a group of formula:

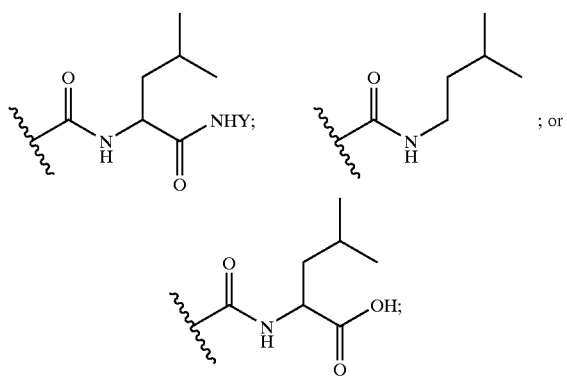

where Y is hydrogen, an alkyl group containing 1 to 6 carbon atoms, or a cycloalkyl group containing 3 to 8 carbon atoms;

each of the stereocenters a and b is independently in the R configuration or the S configuration;

p is 1 or 2; and

X is selected from hydroxyl, and —O—$C_{1-6}$ alkyl groups;

provided that if B is hydrogen or lower alkyl, D is not also hydrogen, and if D is hydrogen B is an aralkyl group.

2. A compound, salt or ester according to claim 1 wherein the stereochemistry at group A is as shown:

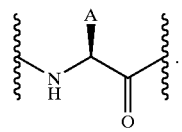

3. A compound, salt or ester according to claim 2, wherein B is hydrogen or a lower alkyl group and D is one of the substituents

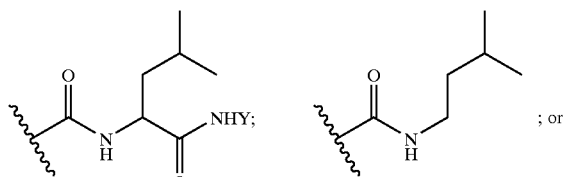

-continued

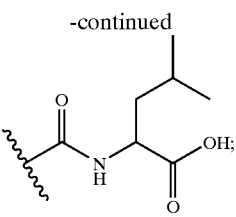

where Y is hydrogen, an alkyl group containing 1 to 6 carbon atoms, or a cycloalkyl group containing 3 to 8 carbon atoms.

4. A compound according to claim 3 having the formula (II) or (II'), or a pharmaceutically acceptable salt or ester thereof:

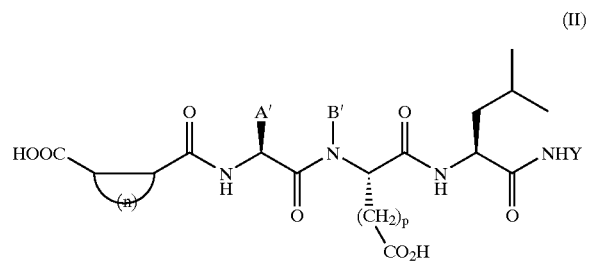
(II)

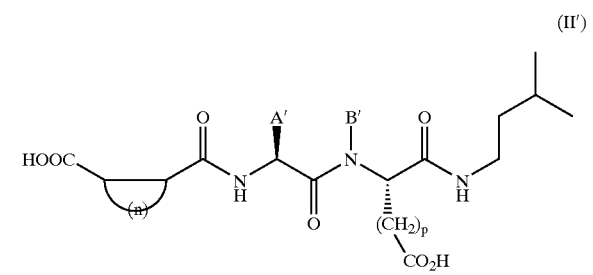
(II')

wherein:

represents a benzene ring or a non-aromatic carbocyclic ring and (n) is the total number of carbon atoms in the carbocyclic ring and is from 4 to 8;

Y is hydrogen, an alkyl group containing 1 to 6 carbon atoms, or a cycloalkyl group containing 3 to 8 carbon atoms;

p is 1 or 2;

B' is hydrogen or lower alkyl; and

A' is cyclohexylmethyl-, phenyl, o-fluorophenyl or p-chlorophenyl.

5. An enantiomer or diastereomer of a compound, salt or ester according to claim 4, or a mixture of enantiomeric and/or diastereomeric forms of said compound, salt or ester.

6. A compound, salt or ester according to claim 1, wherein D is hydrogen and B is an aralkyl group in which the aryl is optionally substituted with from 1 to 3 substituents independently selected from chloro, fluoro, methyl, $CF_3$, $OCH_3$ and $OCF_3$.

7. A compound, salt or ester according to claim 6 wherein the aralkyl group B is a group of formula:

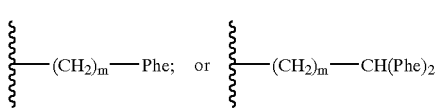

; or where m is 1 or 2, and Phe is phenyl optionally substituted with from 1 to 3 substituents independently selected from chloro, fluoro, methyl, $CF_3$, $OCH_3$ and $OCF_3$.

8. A compound, salt or ester according to claim 7 wherein the group B is selected from:

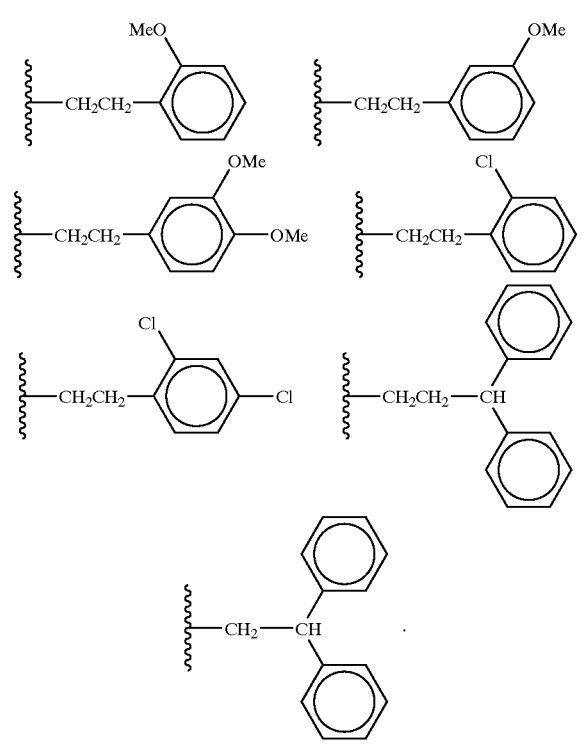

9. A compound according to claim 7 having the formula (III), or a pharmaceutically acceptable salt or ester thereof:

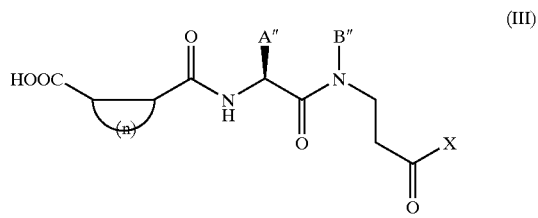
(III)

wherein

represents a benzene ring or a non-aromatic carbocyclic ring and (n) is the total number of carbon atoms in the carbocyclic ring and is from 4 to 8, B" is an aralkyl group in which the aryl is optionally substituted with from 1 to 3 substituents independently selected from chloro, fluoro, methyl, $CF_3$, $OCH_3$ and $OCF_3$ and A" is cyclohexylmethyl-, phenyl, p-bromophenyl, p-trifluoromethylphenyl or o-fluorophenyl.

10. An enantiomer of the compound, salt or ester of claim 9, or a mixture of said compound, salt or ester with its enantiomer.

11. A compound, salt or ester according to claim 1 wherein the group

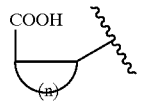

is selected from

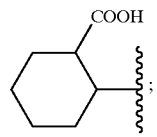 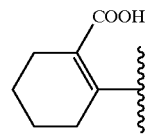 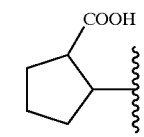 and

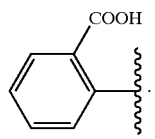

12. A compound, salt or ester according to claim 11 wherein the carbocyclic ring is a cyclohexyl or cyclopentyl ring whose substituents are trans to each other.

13. A compound, salt or ester according to claim 12 wherein the stereochemistry in the carbocyclic ring is 1R, 2R.

14. A compound selected from the group consisting of:
a compound of formula (IV):

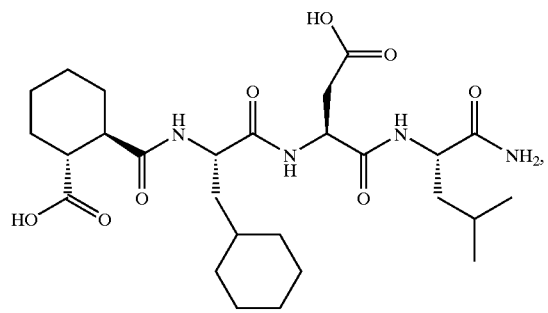

wherein the chiral centers are in the configuration R, R, S, S, S;
a compound of formula (V):

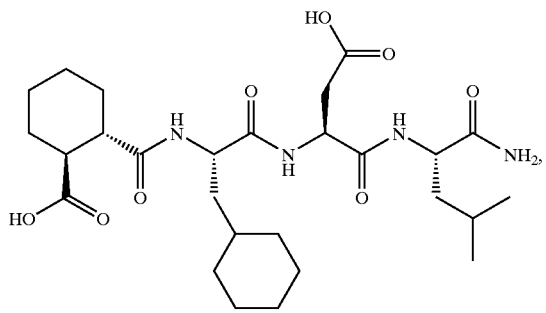

wherein the chiral centers are in the configuration S, S, S, S, S;
a compound of formula (VI):

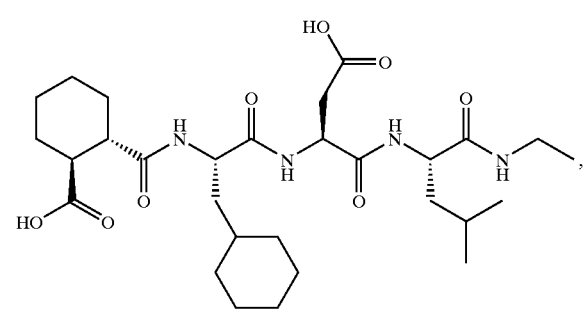

wherein the chiral centers are in the configuration R, R, S, S, S;
and pharmaceutically acceptable salts and esters thereof.

15. A compound selected from the group consisting of:
a compound of formula (VII):

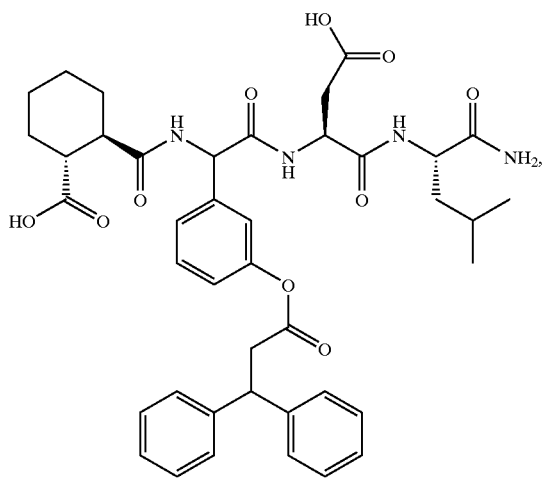

wherein the chiral centers are in the configuration R, R, [R/S], S, S;
a compound of formula (VI):

(VIII)

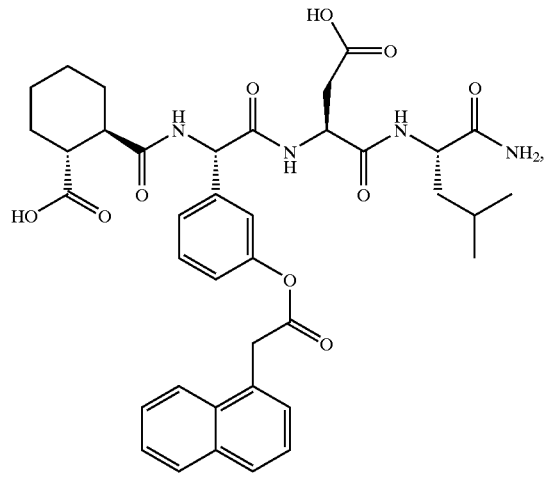

wherein the chiral centers are in the configuration R, R, S, S, S;

a compound of formula (IX):

(IX)

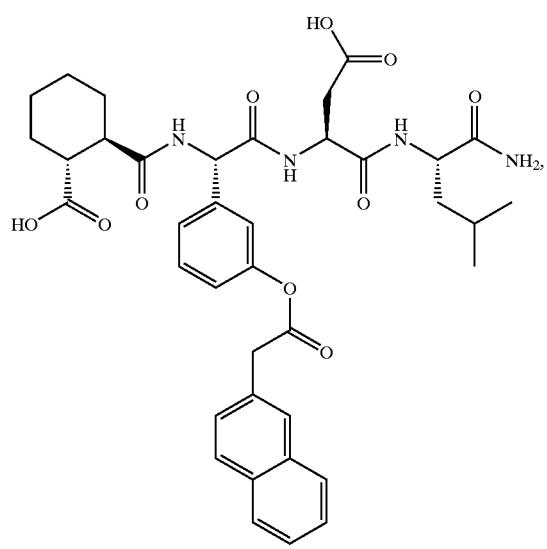

wherein the chiral centers are in the configuration R, R, S, S, S;
and pharmaceutically acceptable salts and esters thereof.

16. A compound selected from the group consisting of:
a compound of formula (X):

(X)

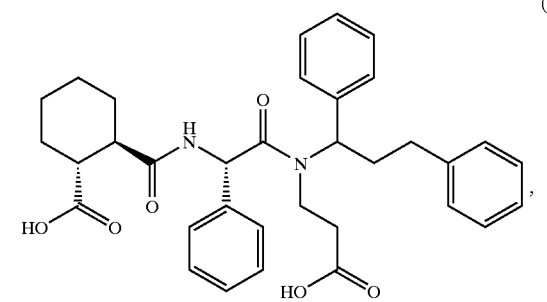

wherein the chiral centers are in the configuration R, R, S;
a compound of formula (XI):

(XI)

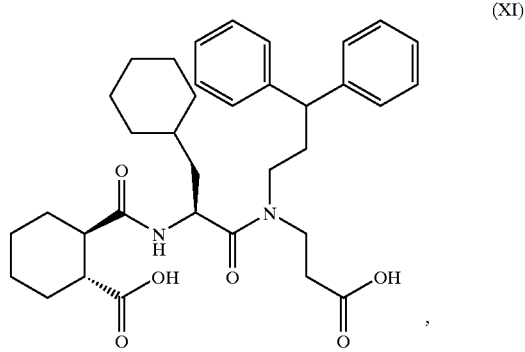

wherein the chiral centers are in the configuration R, R, S;
a compound of formula (XII):

(XII)

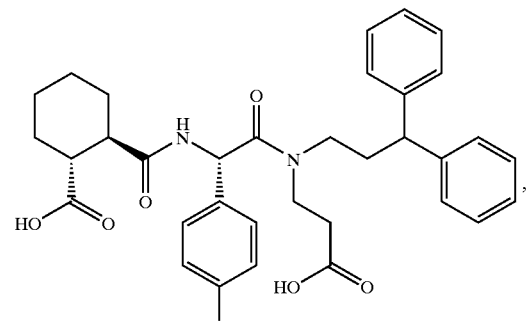

wherein the chiral centers are in the configuration R, R, S;
a compound of formula (XIII):

(XIII)

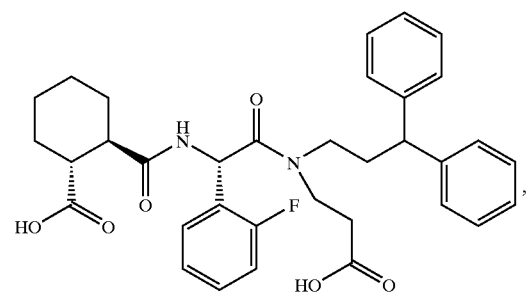

wherein the chiral centers are in the configuration R, R, S;
a compound of formula (XIV):

(XIV)

wherein the chiral centers are in the configuration R, R, S;

and pharmaceutically acceptable salts and esters thereof.

17. A pharmaceutical composition comprising a compound, salt or ester of claim 1 and carrier.

18. A method of inhibiting HCV NS3 protease activity, which comprises administering to a human or animal subject in need of such inhibition an effective amount of a composition according to claim 17.

19. A method of preparation of a pharmaceutical composition, which comprises admixing one or more compounds, salts or esters according to claim 1 with one or more pharmaceutically acceptable excipients, diluents, or carriers.

20. A method for the preparation of a compound according to claim 1 comprising condensing a diacid of formula:

or an activated form thereof, with a suitably protected molecule of formula:

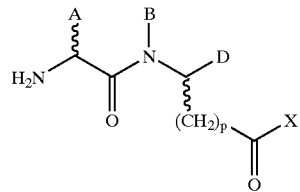

where n, A, B, D, p and X are as defined in claim 1.

21. A method of treating hepatitis C or a related condition, which comprises administering to a human or animal subject suffering from the condition a therapeutically effective amount of a composition according to claim 17.

22. A method of inhibiting HCV NS3 protease activity, which comprises administering to a human or animal subject in need of such inhibition an effective amount of a compound, salt or ester according to claim 1.

23. A method of treating or preventing hepatitis C or a related condition, which comprises administering to a human or animal subject suffering from the condition a therapeutically effective amount of a compound, salt or ester according to claim 1.

* * * * *